United States Patent [19]

Heinrich et al.

[11] Patent Number: 4,954,634
[45] Date of Patent: Sep. 4, 1990

[54] PROCESS FOR THE SELECTIVE N-ACYLATION OF AMINOHYDROXAMIC ACID DERIVATIVES AND STARTING MATERIALS USED THEREIN

[75] Inventors: Peter Heinrich, Binningen; Theophile Moerker, Füllinsdorf, both of Switzerland

[73] Assignee: Ciba-Geigy Corporation, Ardsley, N.Y.

[21] Appl. No.: 221,953

[22] Filed: Jul. 20, 1988

[30] Foreign Application Priority Data

Jul. 23, 1987 [CH] Switzerland ................... 2792/87

[51] Int. Cl.$^5$ ........................................... C07D 233/54
[52] U.S. Cl. ..................................... 548/341; 558/30; 560/148; 560/159; 560/169; 562/623; 260/404.5
[58] Field of Search ................. 560/148, 159, 169; 556/410, 419; 558/30; 260/404.5; 562/623; 548/341

[56] References Cited

U.S. PATENT DOCUMENTS 3,634,407 1/1972 Gaeumann et al. ........... 260/239.3
4,671,901 6/1987 Green ............................ 260/404.5
4,764,523 8/1988 Heinrich ........................... 514/18

FOREIGN PATENT DOCUMENTS 271443 3/1987 European Pat. Off. .
300969 7/1988 European Pat. Off. .
1163337 2/1964 Fed. Rep. of Germany .
1186076 1/1965 Fed. Rep. of Germany .
86/03745 7/1986 PCT Int'l Appl. .

OTHER PUBLICATIONS

Houben-Weyl, Methoden Der Organischen Chemie XIII/5 (1980).
Heuchel et al, Chemiker-Zeitung vol. 107, No. 2 p. 69 (1983).
Journal of Synthetic Organic Chemistry pp. 418–420 (4/87).

Primary Examiner—Michael L. Shippen
Attorney, Agent, or Firm—JoAnn Villamizar

[57] ABSTRACT

Described is a novel process for the introduction of an organic acyl radical selectively at the nitrogen atom of the amino group of desferrioxamine B or of a partially O-acylated derivative thereof. It comprises treating a derivative of desferrioxamine B, in which the amino nitrogen and the hydroxy oxygen of at least one of the hydroxamic acid groupings carries an organic silyl group, with an organic acylating agent and then removing the silyl groups present. The novel N- and O-silylated starting materials can be manufactured, preferably in situ, by reacting an appropriate derivative of desferrioxamine B that has at least one hydroxy group and the amino group in free form, with an organic silicon halide.

10 Claims, No Drawings

PROCESS FOR THE SELECTIVE N-ACYLATION OF AMINOHYDROXAMIC ACID DERIVATIVES AND STARTING MATERIALS USED THEREIN

The present invention relates to a novel process for the introduction of an organic acyl radical selectively at the nitrogen atom of the amino group of desferrioxamine B or of a partially O-acylated derivative thereof. The introduction of the N-acyl radical in accordance with the invention is carried out by treating a derivative of desferrioxamine B, in which the amino nitrogen and the hydroxy oxygen of at least one of the hydroxamic acid groupings carries an organic silyl group, with an organic acylating agent and then removing the silyl groups present. The invention also relates to the silylated starting materials and to the process for the manufacture thereof, preferably in combination with the above-mentioned process.

Desferrioxamine B, the basic material of the acylation process of the present invention, has already been known for a relatively long time (H. Bickel, H. Keberle and E. Vischer: Helv. Chim. Acta 46, 1385–9 [1963]). Its chemical structure corresponds to the formula

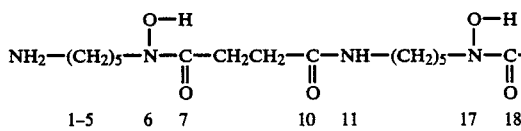 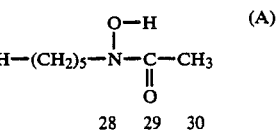 (A)

and, in accordance with rule C-06 (replacement nomenclature) of the official IUPAC nomenclature, it has the systematic name 6,17,28-trihydroxy-7,10,18,21,29-pentaoxo-6,11,17,22,28-pentaazatriacontylamine. (For the sake of simplicity, however, hereinafter the names of the derivatives are derived from the trivial name the position of individual substituents in each case being related to the amino nitrogen N or to the oxygen atoms, designated O, O' and O", of the hydroxy groups in positions 6, 17 and 28, respectively).

One of the most striking properties of desferrioxamine B and its addition salts, which are formed with one equivalent of acid, is the ability to link up with trivalent metal ions, such as chromium(III), aluminium and especially iron(III) ions, to form stable metal complexes or stable chelate-like adducts. This imparts to desferrioxamine B the valuable pharmacological property of preventing the deposit of iron-containing pigments in tissue and, where there are existing deposits of iron in the organism, of causing excretion of the iron, for example in the case of haemochromatosis, haemosiderosis, cirrhosis of the liver and poisoning with compounds of trivalent iron. The broad therapeutic use of desferrioxamine B and its salts (for example especially methanesulfonate) therefore extends generally to diseases and pathological conditions of the human body (and of the bodies of other warm-blooded animals) that are associated with excessive loading of the organism with iron-(III) ions ($Fe^{+++}$ ions), such as thalassaemia major, sickle cell anaemia, sideroachrestic anaemia, aplastic anaemia and other forms of anaemia in which haemosiderosis (that is to say a local or general increase in iron levels in otherwise undamaged body tissue) is involved. This also includes pathological conditions that develop in patients after repeated blood transfusions or repeated dialysis treatment where the kidney function is impaired or has failed completely. Owing to its complex-forming properties, desferrioxamine B has proved to have a significant activity in the case of diseases caused by iron(III)-dependent microorganisms and parasites, such as, especially, malaria, which is of great importance not only in human medicine but also in veterinary medicine. Also, its formation of complexes with other trivalent metals can be used for the excretion of those metals from the organism, for example for the removal of aluminium in the case of dialysis encephalopathy and osteomalacia, and in the case of Alzheimer's disease.

With such a large number of possible uses, attempts are obviously being made specifically to modify appropriately for individual areas of use, and to increase, the favourable physiological properties of desferrioxamine B as a basic material. One possible method is especially the chemical modification of the accessible functional groups, that is to say the terminal amino group and/or the hydroxy groups of the 3-hydroxamic acid groupings, in which process it would be especially desirable to be able to differentiate between the two types of functional groups and selectively functionalize only one type of functional group. For several reasons acylation is one of the modifications in greatest demand. For the vast majority of acyl radicals, however, introduction is not selective. In contrast to aminocarboxylic acids, aminohydroxamic acids and especially aminooligohydroxamic acids, such as desferrioxamine B, cannot as a rule be monoacylated selectively at the amino group by known direct acylation methods (for example according to Schotten-Baumann). The use of equimolar amounts of slight excesses of acylating agent generally results in mixtures that are very difficult to separate and from which only a poor yield of the desired N-acyl derivative can be obtained. An isolated exception to this rule is presented by certain acylating agents that introduce an oxycarbonyl radical, such as the tert.-butoxycarbonyl radical, such as di-tert.-butyl-dicarbonate, and with such agents a substantially selective N-acylation of desferrioxamine B is possible under specific reaction conditions. To produce N-monoacyl derivatives of desferrioxamine B with "normal" acyl radicals, that is to say acyl radicals other than specific oxycarbonyl radicals, the following processes are therefore applied in accordance with the State of the Art:

By using excess acylating agent, first of all N,O,O', O"-tetraacyl derivatives are prepared; N-monoacylates can be obtained therefrom by selective ammonolysis, which involves substantial losses, and laborious separation of the resulting mixtures of substances. From the economic point of view, another important consideration is that, depending on the nature of the acylating agent, only ¼ of that agent is utilized.

If the acyl group used is a suitable acidolytically or hydrogenolytically removable esterified oxycarbonyl group (such as tert.-butoxycarbonyl or benzyloxycarbonyl), such as N-monoacylate can be acylated at the free hydroxy groups with another acid and the N-protecting acyl group can be removed to yield O,O',O"-triacylates having a free amino group. By N-acylation of the resulting O,O',O"-triacylates it is possible to obtain N,O,O',-O"-tetraacylates with different acyl radicals at the nitrogen atom on the one hand and at the oxygen atoms on the other hand. The manufacture of O-unsubstituted N-acylates with any acyl radicals other than oxycarbonyl radicals is not, however, possible, using the last-mentioned process.

In another method, the hydroxamic acid functions of desferrioxamine B are protected against acylation by preliminary complexing with $Fe^{3+}$ or $Al^{3+}$. Such complexing, however, also reduces the reactivity of the amino group. Consequently the subsequent acylation reaction is slow and produces an unsatisfactory yield. The metal ion then has to be removed again in an additional reaction step.

Since the manufacture of an N-monoacylate by the hitherto known methods is complicated and provides only very unsatisfactory results, there is a pressing need for a simple method that can be used for all types of acyl radical, renders possible the selective introduction of an N-acyl group into desferrioxamine B in a simple manner and in high yields and results in pure products.

According to the invention the solution to this problem is based on the surprising observation that a novel derivative of desferrioxamine B, protected by organic silyl groups at the amino nitrogen atom and at the hydroxy oxygen atoms, surprisingly reacts with a wide range of conventional organic acylating agents under customary reaction conditions, and in such a manner that the N-silylated amino group is acylated selectively whereas the hydroxy groups silylated at the oxygen atoms remain unaffected. Since the required novel N- and O-silyated starting materials can be produced simply and virtually quantitatively from the unsubstituted basic compound and because the O-silyl groups can be removed easily, for example by mold solvolysis, the process according to the invention has all the advantages that were missing from earlier proposals. The yield and degree of purity of the desired compounds achieved are so high that is has even proved to be considerably more advantageous to prepare an N,O,O',O"-tetraacyl derivative of desferrioxamine B with four identical acyl radicals indirectly, by way of the mono-N-acyl derivative obtainable in accordance with the process of the invention, instead of by way of direct tetracylation of desferrioxamine B.

The process according to the invention is carried out especially by reacting a compound of formula II

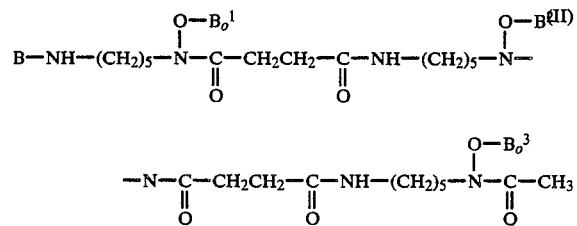

in which B is an organic silyl group (Sil) of formula

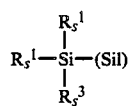

wherein $R_s^1$ and $R_s^2$, independently of one another, are each unsubstituted $C_{1\text{-}8}$-hydroxycarbyl and $R_s^3$ is unsubstituted $C_{1\text{-}8}$-hydrocarbyl or chlorine, and at least one of the symbols $B_o^1$, $B_o^2$ and $B_o^3$ is an organic silyl group Sil and the others are each, independently of one another, Sil or an organic acyl radical Ac, with an agent that introduces an acyl radical Ac, and removing the O-bonded silyl groups Sil present by means of solvolysis.

The compounds obtainable by the process according to the invention are especially those of formula

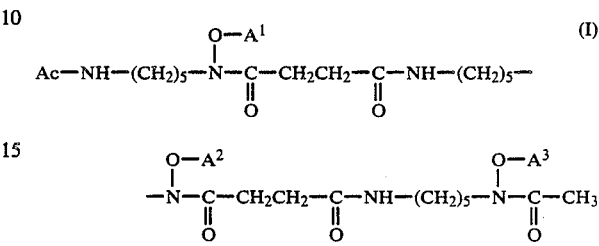

in which Ac has the meaning given above and at least one of the symbols $A^1$, $A^2$ and $A^3$ is hydrogen and the others, independently of one another, are each an acyl radical AC as defined hereinafter.

In preferred starting materials of formula II B, $B_o^1$, $B_o^2$ and $B_o^3$ are all an organic silyl group Sil of the same meaning. In this case the product obtained in an N-monoacylate of desferrioxamine B of formula I in which $A^1$, $A^2$ and $A^3$ are each hydrogen.

The hydrocarbyl radicals $R_s^1$ and $R_s^2$ present in the organic silyl group Sil are especially $C_{1\text{-}8}$-alkyl radicals, for example hexyl, 4-methylpentyl, pentyl, ethyl and, especially, methyl, and also aryl and aralkyl radicals, for example phenyl or p-tolyl and benzyl or phenethyl, respectively; the two radicals are preferably identical. The symbol $R_s^3$ may be chlorine or have one of the meanings mentioned for the symbols $R_s^1$ and $R_s^1$, all 3 symbols preferably having the same meaning; $R_s^3$ is especially methyl.

a suitable organic silyl group Sil is, for example, tributylsilyl, tribenzylsilyl, phenyl-dimethylsilyl, benzyzl-dimethylsilyl, hexyl-dimethylsilyl, tert.-butyl-dimethylsilyl, triethylsilyl, diethyl-chlorosilyl and, especially, dimethyl-chlorosilyl and, more especially, trimethyl-silyl.

The organic acyl radical Ac is derived from a carboxylic acid that may be functionally modified, an organic sulfonic acid or an esterified phosphoric acid and preferably has a maximum of 40 carbon atoms.

An acyl radical Ac derived from a carboxylic acid is especially one of the partial formula $Z-X-C(=O)-$ ($Ac^1$) in which X is a single bond, oxy or unsubstituted or substituted imino and Z is hydrocarbyl $R^o$ or, if X is a single bond, also hydrogen, chlorine or 1-imidazolyl. Depending on the meaning of X, the acyl radicals are derived from hydrocarbylcarboxylic acids, from monoesters or monoamides of carbonic acid, or from formic acid (formyl), chloroformic acid (chloroformyl) or 1-imidazolylcarboxylic acid.

Acyl radicals of hydrocarbylcarboxylic acids are characterised especially by the partial formula $R_b^o-C(=O)-$ ($Ac_a^1$), in which $R_b^o$ is either hydrogen (and thus forms the formyl radical) or hydrocarbyl $R^o$ (and thus forms the radical of an unsubstituted or substituted acyclic, carbocyclic, carbocyclic-acyclic, heterocyclic or heterocyclic-acyclic monocarboxylic acid).

Hydrocarbyl $R^o$ is an acyclic (aliphatic), carbocyclic or carbocyclicacylic hydrocarbon radical that in total has up to 60, preferably a maximum of 40, and especially a maximum of 20, carbon atoms and may be saturated or unsaturated, unsubstituted or substituted. Instead of one, two or more carbon atoms it may alternatively contain identical or different hetero atoms in the acyclic and/or cyclic moiety, such as, especially, oxygen, sulfur and nitrogen; in the latter case it is designated as a heterocyclic radical (heterocyclyl radical) or a heterocyclic-acyclic radical.

Unsaturated radicals are those that contain one or more multiple bonds (double and/or triple bonds). Cyclic radicals in which at least one 6-membered carbocyclic or 5- to 8-membered heterocyclic ring contains the maximum number of non-cumulated double bonds are designated as aromatic. Carbocyclic radicals in which at least one ring is in the form of a 6-membered aromatic ring (that is to say benzene ring) are designated as aryl radicals.

Unless indicated otherwise, in the present disclosure organic radicals designated "lower" contain a maximum of 7, preferably a maximum of 4, carbon atoms.

An acyclic hydrocarbon radical is especially a straight or branched lower alkyl, lower alkenyl, lower alkadienyl or lower alkynyl radical. Lower alkyl is, for example, methyl, ethyl, n-propyl, isopropyl, n-butyl, isobutyl, sec.-butyl or tert.-butyl, or also n-pentyl, isopentyl, n-hexyl, isohexyl or n-heptyl; lower alkenyl is, for example, allyl, propenyl, isopropenyl, 2- or 3-methallyl or 2-or 3-butenyl; lower alkynyl is, for example, propargyl or 2-butynyl. An acyclic hydrocarbon radical is especially also a straight alkyl or alkenyl radical having from 10 to 20 carbon atoms.

A carbocyclic hydrocarbon radical is especially a mono-, bi- or polycyclic cycloalkyl, cycloalkenyl or cycloalkadienyl radical, or a corresponding aryl radical containing aromatic rings. Radicals having a maximum of 12 ring carbon atoms and containing 3-to 8-membered, preferably 5- to 7-membered, especially 6-membered, rings are preferred, it also being possible for them to carry one or more acyclic radicals, for example those mentioned above, and especially the lower alkyl radicals, or other carbocyclic radicals. Carbocyclic-acyclic radicals are those in which an acyclic radical, especially one having a maximum of 7, preferably a maximum of 4, carbon atoms, such as especially methyl, ethyl or vinyl, carries one or more carbocyclic, optionally aromatic radicals of the above definition. Mention may be made especially of cycloalkyl-lower alkyl and aryl-lower alkyl radicals, and also analogues thereof unsaturated in the ring and/or chain, that carry the ring at the terminal carbon atom of the chain.

Cycloalkyl is, for example, cyclopropyl, cyclobutyl, cyclopentyl, cyclohexyl, cycloheptyl and cyclooctyl, and also bicyclo[2,2,2]octyl, 2-bicyclo [2,2,1]heptyl and adamantyl, each of which may also be substituted by 1, 2 or more alkyl radicals, especially methyl radicals; cycloalkenyl is, for example, one of the monocyclic cycloalkyl radicals already mentioned that carries a double bond in the 1-, 2- or 3-position. Cycloalkyl-lower alkyl or -lower alkenyl is, for example, a methyl, 1- or 2-ethyl, 1- or 2-vinyl, 1-, 2- or 3-propyl or allyl radical that is substituted by one of the above-mentioned cycloalkyl radicals, those radicals substituted at the end of the linear chain being preferred. An aryl radical is especially a phenyl radical, or also a naphthyl radical, such as 1- or 2-naphthyl, a biphenylyl radical, such as, especially, 4-biphenylylo, and also an anthryl, fluorenyl or azulenyl radical, or an analogue thereof with one or more saturated rings. Preferred aryl-lower alkyl and -lower alkenyl radicals are, for example, phenyl-lower alkyl and phenyl-lower alkenyl having a terminal phenyl radical, such as for example, benzyl, phenethyl, 1-, 2- or 3-phenylpropyl, diphenylmethyl (benzhydryl), trityl or styryl and cinnamyl, respectively, and also 1- or 2-naphthylmethyl. Aryl radicals that carry acyclic radicals are especially o-, m- and p-tolyl and xylyl radicals with variously positioned methyl radicals.

Heterocyclic radicals, including heterocyclic-acyclic radicals, are especially monocyclic, or alternatively bi- or poly-cyclic, aza, thia, oxa, thiaza, oxaza, diaza, triaza or tetraza radicals of aromatic character, as well as corresponding partially or, especially, fully saturated heterocyclic radicals of this kind; such radicals may optionally, for example as in the case of the above-mentioned carbocyclic or aryl radicals, carry other acyclic carbocyclic or heterocyclic radicals and/or may be mono-, di- or poly-substituted by functional groups. The acyclic moiety in heterocyclic-acyclic radicals has, for example, the meaning given in relation to the corresponding carbocyclic-acyclic radicals. If a heterocyclyl radical as a direct substituent $R^o$ is positioned at a hetero atom, such as oxygen or nitrogen its free valency must originate from one of its carbon atoms. Such radicals are specially unsubstituted or substituted monocyclic radicals containing a nitrogen, oxygen or sulfur atom, such as 2-aziridinyl, and especially aromatic radicals of this kind, such as pyrryl, for example 2-pyrryl or 3-pyrryl, pyridyl, for example 2-, 3-or 4-pyridyl, also thienyl, for example 2- or 3-thienyl, or furyl, for example 2-furyl; analogous bicyclic radicals containing a nitrogen, oxygen or sulfur atom are, for example, indoloylo, such as 2- or 3-indoyl, quinolyl, such as 2- or 4-quinolyl, isoquinolyl, benzofuranyl, chromenylo or benzothienyl; preferred monocyclic and bicyclic radicals containing several hetero atoms are for example, imidazolyl, such as 2-imidazolyl, pyrimidinyl, such as 2- or 4-pyrimidinyl, oxazolyl, isoxazolyl or thiazolyl, and benzimidazoylyl, benzoxazolyl or quinazolyl, respectively. Corresponding partially or, especially, fully saturated analogous radicals are also suitable, such as 2-tetrahydrofuryl, 2- or 3-pyrrolidyl, 2-, 3- or 4-piperidyl, and also 2- or 3-morpholinyl, 2- or 3-thiomorpholinyl, 2-piperazinyl and N,N'-bis-lower alkyl-2-piperazinyl radicals. These radicals may also carry one or more acyclic, carbocyclic or heterocyclic radicals, especially those mentioned above. Heterocyclic-acyclic radicals are derived especially from acyclic radicals having a maximum of 7, preferably a maximum of 4, carbon atoms, for example from those mentioned above, and may carry one, two or more heterocyclic radicals, for example those mentioned above, it also being possible for the ring to be bonded to the chain by one of its nitrogen atoms.

As has already been mentioned, a hydrocarbyl radical (including a heterocyclyl radical) $R^o$ may be substituted by one two or more substituents (functional groups) of identical or different kinds; the following substituents are especially suitable: free, etherified and esterified hydroxy groups; mercapto and lower alkylthio groups and unsubstituted or substituted phenylthio groups; halogen atoms, such as chlorine and fluorine but also bromine and iodine; oxo groups that are in the form of formyl (that is to say aldehydo) and keto groups, and also in the form of corresponding acetals and ketals; azido and nitro groups; primary, secondary and, preferably, tertiary amino groups, primary or secondary amino groups protected by conventional protecting groups, acylamino groups and dicylamino groups, and also optionally functionally modified sulfo groups such as sulfamoyl groups or sulfo groups in salt form. None of these functional groups may be positioned at the carbon atom from which the free valency to a hetero atom, such as especially oxygen, sulfur or nitrogen, originates; preferably, they are separated from this free valency (and thus from the hetero atom) by two or more carbon atoms. The hydrocarbyl radical may also carry free and functionally modified carboxy groups, such as carboxy groups present in salt form or esterified carboxy groups; carbamoyl, ureidocarbonyl or guanidinocarbonyl groups optionally carrying one or two hydrocarbon radicals; and cyano groups.

An etherified hydroxy group present as a substituent in the hydrocarbyl radical is, for example, a lower alkoxy group, such as a methoxy, ethoxy, propoxy, isopropoxy, butoxy or tert.-butoxy group, which may also be substituted. For example, such a lower alkoxy group may be substituted by halogen atoms, especially in the 2-position, such as in the 2,2,2-trichloroethoxy, 2-chloroethoxy or 2-iodoethoxy radial, or by lower alkoxy radicals, especially in the 2-position, such as in the 2-methoxyethyoxy radical. An especially preferred form of etherified hydroxy group is an oxaalkyl radical in which a preferably linear alkyl contains, instead of several carbon atoms, oxygen atoms that are preferably separated from one another by several (especially 2) carbon atoms, so that they form an optionally repeated group $(-O-CH_2CH_2-)_n-$ in which n=from 1 to 14. Further, such etherified hydroxy groups are also unsubstituted or substituted phenoxy radicals and phenyl-lower alkoxy radicals, such as especially, benzyloxy, benzhydryloxy and triphenylomethoxy (triyloxy), and also heterocyclyloxy radicals, such as, especially, 2-tetrahydropyranyloxy. An especially preferred etherified hydroxy group is the grouping methylenedioxy and ethylenedioxy; the former, as a rule, substitutes 2 adjacent carbon atoms, especially in aryl radicals, and the latter is bonded to one and the same carbon atom and acts as a protecting group of oxo.

An esterified hydroxy group present as a substituent in the hydrocarbyl radical carries an acyl radical $AC^o$ having a maximum of 12 carbon atoms that also, within this total number of carbon atoms, may be substituted analogously to the radical $AC^1$, or is lactonised by a carboxy group also present in the hydrocarbyl radical.

An esterified group present as a substituent in the hydrocarbyl radical is one in which the hydrogen atom has been replaced by one of the above-characterised hydrocarbon radicals, preferably a lower alkyl or phenyl-lower alkyl radial; examples of an esterified carboxy group are especially methoxy-, ethoxy-, tert.-butoxy- and benzyloxy-carbonyl groups, and also lactonised carboxy group.

A primary amino group $-NH_2$ as a substituent of the hydrocarbyl radical may also be in protected form as a corresponding acylamino group of the formula $-NH-Ac^o$ in which $Ac^o$ has the above-characterised meaning. A secondary amino group carries instead of one of the two hydrogen atoms a hydrocarbyl radical, preferably an unsubstituted hydrocarbyl radical, such as one of those mentioned above, but can also be present in a protected form as an acylamino group derived therefrom having a monovalent acyl radical $Ac_a^o$ characterised hereinafter.

The acyl radical $AC_a^o$ acting as amino-protecting group is preferably derived from a carbonic acid semiderivative and is preferably lower alkoxycarbonyl or aryl-lower alkoxycarbonyl each unsubstituted or substituted especially by lower alkyl, lower alkoxy, nitro and/or halogen, such as methoxycarbonyl, ethoxycarbonyl, tert.-butoxycarbonyl, 2,2,2-trichloroethoxycarbonyl, 2-iodoethoxycarbonyl, benzyloxycarbonyl, 2-phenyl-2-propoxycarbonyl, 2-p-tolyl-2-propoxycarbonyl, 2-(p-biphenyl)-2-propoxycarbonyl or 9-fluorenylmethoxycarbonyl).

A tertiary amino group present as a substituent in the hydrocarbyl radical carries 2 different or, preferably, identical hydrocarbyl radicals (including heterocyclic radicals), such as the above-characterised unsubstituted hydrocarbyl radicals.

A preferred amino group is one of the formula

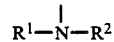

in which $R^1$ and $R^2$, independently of one another are each hydrogen, unsubstituted acyclic $C_1$–$C_7$-hydrocarbyl (such as, especially, $C_{1-4}$-alkyl or $C_1$–$C_4$-alkenyl) or monocyclic unsubstituted or $C_1$–$C_4$-alkyl-, $C_1$–$C_4$-alkoxy-, halo-and/or nitro-substituted aryl, aralkyl or aralkenyl having a maximum of 10 carbon atoms, if being possible for the carbon-containing radicals to be bonded to one another by a carbon-carbon bond or by an oxygen or sulfur atom or by a nitrogen atom that is unsubstituted or substituted by hydrocarbyl. In such a case the radicals form, together with the nitrogen atom of the amino group, a nitrogen-containing heterocyclic ring. The following may be mentioned as examples of especially preferred free amino groups: di-lower alkylamino, such as dimethylamino, diethylamino, pyrrolidino, piperidino, morpholino, thiomorpholino and piperazino or 4-methylpiperazine, or diphenylamino or dibenzylamino unsubstituted or substituted by lower alkyl, lower alkoxy, halogen and/or by nitro; and of the protected amino groups thus, especially, lower alkoxycarbonylamino, such as tert.-butoxycarbonylamino, phenyl-lower alkoxycarbonylamino, such as 4-methoxybenzyloxycarbonylamino, and also 9-fluorenylmethoxycarbonylamino.

A preferred hydrocarbyl radical $R^o$ in the acyl radical $R^o-C(=O)-$ is, for example, $C_1$–$C_{19}$-alkyl, especially such a radical that has a linear chain when there are more than 5 carbon atoms and that may carry the following substituents: a carboxy group that may optionally also be present in salt form or in the form of a cyano group or a $C_{1-C_4}$-alkyl ester ($C_1$–$C_4$-alkoxycarbonyl group), and that is preferably in the ω-position, an amino group of the above-defined formula

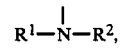

preferably one in which $R^1$ and $R^2$ are each hydrogen in which case the group is preferably in the 1-position, or one or more halogen atoms, especially fluorine or chlorine, which are preferably adjacent to the carbonyl group. Another preferred acyl radical Acla is a bicyclic or, especially, monocyclic aroyl radical, especially benzoyl, that may also carry one or more of the following substituents: halogen atoms, especially chlorine or fluorine, nitro groups, $C_1$–$C_4$-alkyl radicals, especially methyl, hydroxy groups and etherified hydroxy groups, especially $C_1$–$C_4$-alkoxy, such as methoxy, phenoxy and methylenedioxy, and also carboxy groups that may also be present in salt form or in the form of a cyano group or a $C_1$–$C_4$-alkyl ester ($C_1$–$C_4$-alkoxycarbonyl). Preferably, the aroyl radicals carry no more than 2 such substituents, and especially carry only one. Also preferred are analogous heteroaroyl radicals, especially those that are derived from pyridine, furan, thiophene and imidazole, and from the analogues thereof with a fused benzo ring (such as quinoline, isoquinoline, benzofuran and benzimidazole) and that are also unsubstituted or substituted as indicated above. Preferred acyl radicals of this kind are also derived from benzyl and styryl (that is to say phenacetyl and cinnamoyl), and may also be substituted in the manner indicated above.

Such acyl radicals $Ac_a^1$ form, together with the amino nitrogen of desferrioxamine B, corresponding acylamides of which those with the above-mentioned meanings of $Ac_a^1$ are especially preferred. Examples are N-acyl derivatives of desferrioxamine B that are derived from the following carboxylic acids: aliphatic monocarboxylic acids having a maximum of 20 carbon atoms, such as lower alkanecarboxylic acids, for example propionic, butyric, isobutyric, valeric, isovaleric, caproic, trimethylacetic, oenanthic and diethylacetic acid and, especially, acetic acid, as well as lauric, myristic, palmitic and stearic acid and also oleic acid, elaidic acid, linoleic acid and linolenic acid, but also corresponding halogenated lower alkanecarboxylic acids, such as chloroacetic acid, bromoacetic acid or α-bromoisovaleric acid, carbocyclic and carbocyclicacyclic monocarboxylic acids, for example cyclopropane-, cyclopentane- or cyclohexane-carboxylic acid, and cyclopentane-or cyclohexane-acetic acid or -propionic acid, respectively; aromatic carbocyclic carboxylic acids, for example benzoic acid, that may be mono- or poly-substituted in the manner indicated above; aryl- or aryloxy-lower alkanecarboxylic acids and the analogues thereof unsaturated in the chain, for example phenylacetic and phenoxyacetic acids, phenylpropionic acids and cinnamic acids each unsubstituted or substituted in the manner indicated above for benzoic acid; and heterocyclic acids, for example furan-2-carboxylic acid, 5-tert.-butylfuran-2-carboxylic acid, thiophene-2-carboxylic acid, nicotinic or isonicotinic acid, 4-pyridinepropionic acid, and pyrrole-2-or -3-carboxylic acids unsubstituted or substituted by lower alkyl radicals; also corresponding α-amino acids, especially the naturally occurring α-amino acids of the L-series, for example glycine, phenylglycine, proline, leucine, valine, tyrosine, histidine and asparagine, preferably in an N-protected form, that is to say in a form in which the amino group is substituted by a conventional amino-protecting group, for example one of the above-mentioned amino-protecting groups; and also dicarboxylic acids, such as oxalic acid, malonic acid, mono- or di-lower alkylmalonic acids, succinic acid, glutaric acid, adipic acid, erucic acid, maleic acid, a phthalic, quinolinic, isoquinolinic or phenylsuccinic acid unsubstituted or substituted by halogen, such as fluorine, chlorine or bromine, and/or by lower alkyl, hydroxy, lower alkoxy and by nitro, as well as, also glutamic acid and aspartic acid, the last two acids preferably having protected amino groups. As has already been stated, the second carboxy group may be either free or functionally modified, for example in the form of a $C_1$–$C_4$-alkyl ester or a salt, preferably a physiologically tolerable salt, with a salt-forming basic component. There are suitable especially metal or ammonium salts, such as alkali metal and alkaline earth metal salts, for example sodium, potassium, magnesium or calcium salts, and ammonium salts with ammonia or suitable organic amines.

An acyl radical $Ac_b^1$ derived from monoesters of carbonic acid is characterised by the partial formula $R^o$—O—CO—. With the basic structure of desferrioxamine B this acyl radical thus forms corresponding N-mono-substituted urethanes. Such acyl radicals are, for example, those in which Ro has the following preferred meanings of an acyclic hydrocarbyl radical: $C_1$–$C_{20}$-alkyl, $C_2$–$C_{20}$-hydroxyalkyl in which the hydroxy group is in any position except the 1-position, but is preferably in the 2-position, cyano-[$C_1$–$C_{20}$]-alkyl in which the cyano group is preferably in the 1- or ω-position, or carboxy-[$C_1$–$C_{20}$]-alkyl in which the carboxy group is preferably in the 1- or ω-position and may optionally also be in salt form or in the form of a $C_1$–$C_4$-alkyl ester ($C_1$–$C_4$-alkoxycarbonyl) or benzyl ester (benzyloxycarbonyl), and also $C_1$–$C_{20}$-alkenyl, the free valency of which is not at the same carbon atom as the double bond, all of the radicals mentioned, apart from those with the $C_3$–$C_5$-alkyl basic structure, containing a linear (unbranched) alkyl chain; as well as, also, a linear (mono- or di- to hexa-)-oxaalkyl having from 4 to 20 chain members, wherein one or more of the carbon atoms, from C-3 on, of a linear $C_4$–$C_{20}$-alkyl have been replaced by oxygen atoms that are separated from one another by at least 2 carbon atoms and are preferably in positions 3, 6, 9, 12, 15 and 18. Radicals of formula —(CH$_2$—CH$_2$—O—)$_n$-lower alkyl, in which n is 1 to 19, especially, are preferred. There may also be mentioned radicals $Ac_b^1$ in which $R^o$ has the following preferred meanings of a carbocyclic or heterocyclic, or also carbocyclic-acyclic or heterocyclic-acyclic hydrocarbyl radical: bicyclic or preferably monocyclic aryl, especially phenyl, that may carry one or more of the following substituents: halogen atoms, especially fluorine and chlorine, $C_1$–$C_4$-alkyl radicals, especially methyl, $C_1$–$C_4$-alkoxy groups, especially methoxy, methylenedioxy, nitro groups and/or carboxy groups, that may be free, in a salt form or in the form of $C_1$–$C_4$-alkyl esters, especially methoxycarbonyl or ethoxycarbonyl. Preferably the aryl radicals carry no more than 2 substituents, especially substituents of the same kind, or only one substituent; they are more especially unsubstituted. A preferred heterocyclic hydrocarbyl (heterocyclyl) radical is, for example, one that is analogous to the aryl radicals given special mention above and contains instead of one or two carbon atoms in each case a hetero atom, especially nitrogen, such as a pyridyl or quinolyl radical, or a quinazolyl radical, the free valency being located at a carbon atom. Preferred carboxyclic-acyclic and heterocyclic-acyclic hydrocarbyl radicals are those in which two or three, but preferably only one, of the above-defined cyclic radicals, preferably the unsubstituted ones, are(is) carried by $C_1$–$C_3$-alkyl, all of then preferably being located at a carbon atom, preferably the terminal carbon atom; unsubstituted benzyl is most preferred.

Especially preferred hydrocarbyl radicals $R^o$ in acyl $Ac_b^1$ are, for example, as follows: acyclic hydrocarbyl, especially $C_1$–$C_{20}$-alkyl, which is preferably linear and may be substituted by a carboxy group that is preferably in functionally modified form, such as in the form of a salt, cyano or a $C_1$–$C_4$-alkyl ester, and preferably in the ω-position, or an analogous linear (mono- to hexa)-oxaalkyl having from 4 to 20 chain members, especially one that has been characterised above as especially preferred. Preferred radicals Ro are also unsubstituted or substituted phenyl and benzyl radicals, for example those mentioned above as being preferred.

Another acyl radical is derived from amides of carbonic acid and is characterised by the formula

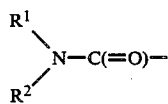 (Ac$_c^1$)

in which $R^1$ and $R^2$ have the meanings given above. With the amino nitrogen of desferrioxamine B this acyl radical thus forms corresponding ureas.

Of the preferred acyl radicals of this kind attention is drawn especially to those in which one of the radicals $R^1$ and $R^2$ is hydrogen and the other is a $C_1$-$C_7$-alkyl radical, preferably a $C_1$-$C_5$-alkyl radical, that may be substituted by hydroxy, mercapto, methylthio, phenyl, p-hydroxyphenyl, p-methoxyphenyl, 2-indolyl, 2-imidazolyl and, especially, by one or more carboxy groups (free or in functionally modified form, such as $C_1$-$C_4$-alkoxycarbonyl, carbamoyl or amidino), one of the free or functionally modified carboxy groups preferably being in the 1-position. This so-substituted $C_1$-$C_7$-alkyl radical preferably corresponds to a radical whose free valency stands in place of the amino group in a common amino acid, such as β-alanine, γ-aminobutyric acid or norvaline, and especially in an α-amino acid of the L-series occurring naturally as a peptide building block, or in an antipode thereof. Especially preferred acyl radicals of the formula Ac$_c^1$ are those in which $R^1$ is hydrogen and $R^2$ is $C_1$-$C_5$-alkyl substituted in the 1-position by $C_1$-$C_4$-alkoxycarbonyl.

An especially preferred acyl radical is the radical of the formula Cl—SO$_2$—NH—CO— (chlorosulfonylaminocarbonyl), which offers interesting possibilities for further functionalisation.

Another organic acyl radical Ac, denoted Ac$^2$, is derived from an acyclic, carbocyclic or heterocyclic, or alternatively a carbocyclic-acyclic or heterocyclic-acyclic sulfonic acid and corresponds to the partial formula R$^o$—O—SO$_2$— or R$^o$—SO$_2$— in which R$^o$ is hydrocarby with the above-mentioned general and, especially, preferred, meanings. Of the compounds of the invention that carry the Ac$^2$ radical, attention is drawn especially to those in which R$^o$ is $C_1$-$C_7$-alkyl, especially linear $C_1$-$C_7$-alkyl, bicyclic or monocyclic aryl, such as especially phenyl, that may be substituted in a manner analogous to that described above for specially mentioned aroyl radicals. Attention is drawn also to analogously constructed bicyclic and monocylic aromatic heterocyclyl radicals in which one or two of the carbon atoms have been replaced by hetero atoms, such as 2- or 4-pyrimidyl, quinolyl or isoquinolyl. Also, the heterocyclyl radicals may carry substituents, especially those to which attention was drawn in the case of aroyl (in thise case, for example, a hydroxy derivative is equivalent to a dihydro-oxo derivative as a result of tautomeric displacement of the double bond). The radical O=C=N—SO$_2$-(isocyanatosulfonyl) may be mentioned as an especially preferred form thereof. Especially preferred acyl radicals of this kind are N-(lower alkoxysulfonyl)-carbamoyl radicals and radicals of the formula lower alkoxy(CH$_2$—CH$_2$—O—)$_n$CO—N-H—SO$_2$—, in which n is from 1 to 19.

Yet another organic acyl radical Ac is the acyl radical Ac$^3$ derived from a phosphoric acid. This is, for example, a hydrocarbyl ester or amide derived from pyrophosphoric acid or, especially, from orthophosphoric acid. Of the acyl groups Ac$^3$ of the invention attention is drawn especially to those of the partial formula

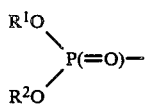

in which $R^1$ and $R^2$ have the above-mentioned general and especially preferred meanings except for hydrogen, are preferably identical, and are each an unsubstituted $C_1$-$C_7$-alkyl radical, especially a linear radical, such as, especially, methyl or ethyl, or a phenyl radical that is unsubstituted or substituted especially by $C_1$-$C_4$-alkyl, $C_1$-$C_4$-alkoxy, halogen and/or by nitro.

Preferably, the acyl radical Ac is $C_2$-$C_{20}$-alkanoyl, benzoyl, $C_{18}$-alkenoyl, ($C_1$-$C_{12}$-alkoxy)-carbonyl, a radical of the formula —CO—O—(CH$_2$—CH$_2$—O—)$_n$-lower alkyl in which n is from 1 to 19, chlorocarbonyl, (1-imidazolyl)-carbonyl, N-di-lower alkylcarbamoyl, ($C_1$-$C_5$-alkyl)-aminocarbonyl substituted in the 1- or 2-position of the alkyl moiety by ($C_1$-$C_4$-alkoxy)-carbonyl, N-(chlorosulfonyl)-carbamoyl, N-(lower alkoxysulfonyl)-carbamoyl, or a radical of formula —SO$_2$—NH—CO(—O—CH$_2$—CH$_2$)$_n$-lower alkoxy in which n is from 0 to 19.

Generally, the reaction products containing chlorocarbonyl, (1-imidazolyl)-carbonyl or N-(chlorosulfonyl)-carbamoyl as acyl radical Ac are in a further reaction step converted with chlorine replacement into different products of formula I in which the acyl radical Ac preferably has one of the other meanings mentioned above.

The agents to be used in accordance with the invention for introducing the acyl radical Ac are acylating agents customarily used for that purpose; those used are espcially acylating agents of the formula AcY (III) in which Ac has the general and preferred meanings given above, for example, for Ac$^1$, Ac$^2$ and Ac$^3$, and Y is a reactive functionally modified hydroxy group or is an additional bond in the radical Ac that replaces hydrogen at the atom α-positioned to the carbonyl group.

An acylating agent derived from the above-defined acyl radical Ac$^1$ of a carboxylic acid is especially one of the formula

Z—X—C(=O)—Y    (IIIA)

in which X and Z have the meanings given above and Y is a reactive functionally modified hydroxy group or is an additional single bond of which the other end replaces a hydrogen atom either in the imino group (if X is —NH—) or at the first carbon atom of the hydrocarbyl radical R$^o$ (if X is a single bond and Z is a suitable hydrocarbyl radical R$^o$).

A reactive funtionally modified hydroxy group is especially an esterified hydroxy group, for example one that is esterified by a strong inorganic acid, such as a hydrohalic acid, for example hydrochloric, hydrobromic or hydriodic acid, a pseudohydrohalic acid, such as azoimide or imidazole (with removal of the H-atom from the 1-N-atom), an oxygen-containing mineral acid, such as phosphoric acid and, especially, sulfuric acid, or by a strong organic acid, such as aliphatic or aromatic sulfonic acid (for example methane- and ethane- or benzene-, p-toluene-, p-nitrobenzene- and p-chlorobenzene-sulfonic acid). Such as esterified group thus forms a mixed anhydride with the acyl radical. Of these mixed anhydrides attention is drawn especially to those with hydrohalic acids and pseudohydrohalic acids, such as acid bromides, acid chlorides, acid azides and 1-imidazolyl derivatives of the formula

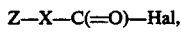

Z—X—C(=O)—Hal, in which Hal is bromine or azido, preferably chlorine or 1-imidazolyl, and Z and X have the meanings given above. Phosgene and its less toxic analogue bis-(1-imidazolyl)-carbon (and similar reagents) may be mentioned as reagents of this type. They are normally used in equimolar amounts so that the second reactive group Y is retained in the product and can be modified subsequently.

Preferred acid chlorides are, inter alia, selected from the following: $C_2$-$C_{20}$alkanoic acid chlorides, benzoyl chloride, $C_{18}$-alkenoic acid chloride, chloroformic acid ($C_1$-$C_{12}$-alkyl)-esters, a chloroformic acid ester of the formula Cl—CO—O—($CH_2$—$CH_2$—O—)$_n$ lower alkyl, in which n is from 1 to 19, and also a chloroformic acid ester of the formula Cl—CO—NH—($C_1$-$C_5$-alkylene)—COO—($C_1$-$C_4$-alkyl).

The reactive esterified hydroxy group can, however, also be esterified either by the radical of another carboxylic acid, especially a stronger carboxylic acid, such as formic acid, chloroacetic acid or, especially, trifluoroacetic acid, and form the basis of a mixed anhydride, or, alternatively, by the same acyl radical and form a symmetrical carboxylic acid anhydride of the formula Ac$^1$—O—Ac$^1$, especially of the formula R$^o$—CO—O—CO—R$^o$ or R$^o$—O—CO—O—CO—R$^o$.

An advantageous meaning of Y in acyl radicals Ac$^2$ and Ac$^3$ is a reactive hydroxy group esterified by strong acids, such as one of those defined above that forms a mixed acid anhydride with the acyl radical. Of these, mixed anhydrides with hydrohalic acids, especially with hydrobromic acid and more especially hydrochloric acid, are especially preferred, that is to say acid bromides and acid chlorides, for example those of the formulae

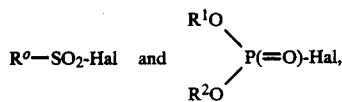

R$^o$—SO$_2$-Hal and $\begin{array}{c}R^1O\\R^2O\end{array}$P(=O)-Hal, in which Hal is bromine and preferably chlorine and R$^o$, R$^1$ and R$^2$ have the meanings given above.

Acylating agents of the formula IIIA in which Y is an additional bond to the radical R$^o$ or —NH— are derived especially from acyl radicals Ac$^1$ of carboxylic acids that carry a hydrogen atom at the atom adjacent to the carbonyl group (that is at the adjacent carbon or nitrogen atom); they belong to the category of ketones or isocyanates, respectively, and correspond to the formulae R$_a$$^o$=C=O and R$^o$—N=C=O in which R$^o$ has the meaning given above and R$_a$$^o$ is a hydrocarbylidene, that is to say a bivalent radical of aliphatic character which corresponds to the radical R$^o$ and in which the functionalised carbon atom is bonded by single bonds to adjacent carbon and/or hydrogen atoms. Chlorosulfonylisocyanate (ClSO$_2$—N=C=O) may be mentioned as a notable agent of this kind. As a rule this is so used that of its two reactive groupings only one, preferably the isocyanato group, reacts; preferably, acylation is carried out with only one equivalent of the agent.

The reaction according to the invention with the acylating agent of the formula III is carried out under process conditions that are generally customary in organic chemistry for the acylation of amines, usually at temperatures of from the freezing point to the boiling point of the reaction mixture, such as in a temperature range of from approximately −10° to approximately +160°, especially from approximately +20° to approximately +50°, at atmospheric pressure or elevated pressure, in heterogeneous phase (such as a suspension) while stirring or shaking or, especially, in homogeneous liquid phase, such as in an excess of liquid reagent or, especially, in the presence of solvents, especially organic solvents, and where appropriate in the presence of acid-binding inorganic or organic agents.

Suitable solvents are, for example, aprotic organic solvents of low polarity, such as halogenated, especially chlorinated, aliphatic hydrocarbons, such as chloroform and dichloromethane, and especially polar aprotic solvents, such as aliphatic and cyclic ethers, for example diethyl ether, 1,2-dimethoxyethane and diisopropyl ether, and dioxan and tetrahydrofuran, respectively, lower aliphatic esters and amides, such as ethyl acetate and formamide, acetamide, N,N-dimethylacetamide and dimethylformamide respectively, and also acetonitrile, dimethyl sulfoxide and hexamethylphosphorus triamide; the solvents may also be used in suitable combinations, for example to increase the solubility of components.

The acid-binding agents used may in principle be any basic compounds such as, on the one hand, organic nitrogen-containing bases, for example tertiary amines of the triethylamine, ethyldiisopropylamine, N,N-dimethylaniline, N-ethylpiperidine or N,N'-dimethylpiperazine type, or aromatic heterocyclic bases of the pyridine, collidine, quinoline or 4-dimethylaminopyridine type, and, on the other hand, inorganic compounds having a basic reaction, such as alkali metal hydroxides, carbonates, and hydrogen carbonates, and also salts of carboxylic acids, such as sodium or potassium acetate. Finally, this function can also be performed by nitrogen-containing compounds having a neutral reaction, which at the same time are often also advantageous solvents, for example carboxylic acid amides, especially lower aliphatic carboxylic acid amides, such as those mentioned above, and cyclic amides, such as N-methylpyrrolidone, and also amido derivatives of carbonic acid, such as urethanes and urea. Conversely, the above-mentioned bases, especially those of the pyridine type, can act as solvents.

Although the acylation reaction is always based on the same principle and the reaction is carried out according to a uniform basic scheme, to obtain an optimum result it is necessary in practice to take into consideration the inherent nature of the reactants, especially that of the reactant of formula III in question.

In acylations with the above-described mixed or alternatively symmetric anhydrides as acylating agents, the reaction is preferably carried out in the presence of an acid-binding agent, such as one of those mentioned above, which is used especially in an equivalent amount or in a small excess (that normally does not exceed 2 equivalents). Acylation with isocyanates can, depending on their nature, also be carried out without acid-binding agents, in which case the exclusion of moisture and/or of protic solvents is recommended.

If the hydrocarbyl radical $R^o$ has been substituted by functional groups that might also react during the acylation, such as free carboxy, hydroxy and, especially amino groups, these are especially temporarily protected or are preferably already in protected form in the acylating agent used and the protecting groups are removed when acylation is complete.

Thus, for example, one of the most common methods of protecting carboxy groups is esterification. An esterified carboxy group is generally freed by conventional hydrolysis, especially under the action of bases (such as, especially, alkali metal hydroxides, carbonates or hydrogen carbonates), or alternatively, in the case of suitable esters, such as those of tertiary alcohols (for example tert.-butyl alcohol), by acidolysis, for example by means of hydrogen fluoride or trifluoroacetic acid. Esters with benzyl alcohols can also be removed by conventional hydrogenolysis.

The groups used for the temporary protection of hydroxy groups and methods for their removal are also generally known, for example from the synthesis of peptides. Hydroxy groups are especially protected in the form of esters with carboxylic acids, such as with lower alkanoic acids or with monoesters of carbonic acid (for example formates or acetates on the one hand or tert.-butoxy- or benzyloxy-carbonates on the other hand), or alternatively in the form of ethers, such as, especially, those of tertiary alcohols (for example tert.-butylalcohol), or in the form of acetals (for example especially in the form of 2-tetrahydropyranyl ether). The former protecting groups are usually removed analogously to esterified carboxy groups; the latter two are removed especially by acidolysis.

The protecting groups that can be used for the temporary protection of primary and secondary amino groups correspond to those that were investigated in detail in the synthesis of peptides and the most widely used. Preferably, the amino-protecting groups mentioned at the beginning are used. Their removal, which generally depends on their specific nature, is carried out under the generally known conditions of solvolysis (especially basic hydrolysis or acidolysis) or hydrogenolysis.

The general conditions for the conventional removal of the functionally modified groups are especially so selected that neither the bond between the acyl radical and the amino group of desferrioxamine B nor the basic structure thereof is affected.

The removal of the O-bonded organic silyl groups to be carried out in accordance with the invention as a second process step is effected according to processes that have been well-developed and are generally customary in organic chemistry for cleaving the silicon-oxygen bond in silyl ethers and silyl esters, especially by solvolysis. The removal can especially be carried out under customary conditions of alcoholysis, for example by treatment with a lower alkanol, especially methanol, preferably in the presence of an acidic catalyst, for example an acid addition salt of an organic base, that is used as reaction solution (such as pyridine hydrochloride). Such a variant has the advantage that readily volatile simple silyl ethers (such as, especially, trimethylsilyl-methyl ether) are formed that can be removed without any problem from the reaction mixture, usually together with the solvent, by distillation.

The invention also relates to those variants of the process of the invention according to which a compound obtainable as an intermediate at any stage of the process is used as starting material and the remaining steps are carried out, and especially to those variants in which the N,O-silylated derivative of desferrioxamine B to be used as starting material is formed under the reaction conditions. Such a derivative is especially formed by treating desferrioxamine B or an acid addition salt thereof (or a corresponding partially O-acylated analogue thereof) with a suitable silylating agent (see further below), especially trimethylchlorosilane or dimethyldichlorosilane, under the conditions described hereinafter, and treated with the acylating agent in the same reaction medium. Since the treatment with the customary silylating agents and also with the acylating agents of the invention are advantageously carried out under analogous conditions, especially in the same solvents, the two kinds of reagent as a rule not reacting with one another, an advantageous form of the process comprises carrying out the acylation according to the invention after the silylation reaction (that is to say the manufacture of the starting material in situ) in the same reaction medium, where appropriate in the presence of an excess of silylating agent. Suitable solvents for this form of process are, for example, the above-mentioned polar aprotic solvents and/or tertiary organic bases, for example pyridine. It is especially also possible to undertake the subsequent removal of the O-bonded silyl groups (and at the same time also the destruction of excess silylation and/or acylating agent) in the same reaction medium, especially by adding a lower alkanol, such as, preferably, methanol, to the reaction mixture after the silylation and acylation steps. In this case, too, the above-described polar aprotic solvents and especially the tertiary organic bases are suitable reaction media. The alcoholysis is further accelerated by the catalytic influence of a strong acid (especially hydrogen chloride), which is formed by the decomposition of the silylation and acylation reagent.

The compounds of formulae III, IIIA and IV used as acylating agents in the process according to the invention are known or can be routinely obtained by generally known manufacturing methods in organic chemistry.

The N,O-silylated derivatives of desferrioxamine B used as starting material, especially those of the above-defined formula II, are novel and the invention relates also to these. Preferred compounds of the above formula II are those in which B, $B_o^1$, $B_o^2$ and $B_o^3$ all have the same meaning and represent one of the initially defined organic silyl radicals Sil, especially those in which B is tri-$(C_1-C_6$alkyl$)$-silyl, especially trimethylsilyl or also dimethylchlorosilyl.

The compounds can be obtained according to processes known per se that are generally customary for the N- and O-silylation of organic compounds. The corresponding process for their manufacture, to which this invention also relates, is carried out, for example, by reacting desferrioxamine B (also in the form of a salt thereof) or a partially O-acylated derivative thereof, especially a compound of the general formula

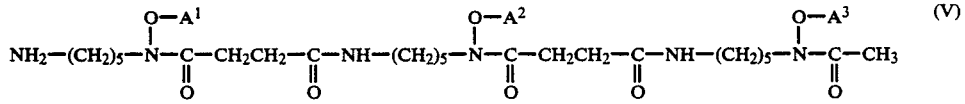

in which at least one of the symbols $A^1$, $A^2$ and $A^3$ is hydrogen and the others, independently of one another, are each hydrogen or the radical Ac with the above-defined meaning, with a silylation reagent of formula Sil-Hal (VI), in which Sil is as defined initially and Hal is bromine, or especially chlorine.

Also, compounds in which the symbols Sil and Ac have the meanings given special mention at the beginning are preferred here, such as, on the one hand, desferrioxamine B of formula V in which $A^1$, $A^2$ and $A^3$ are each hydrogen and, on the other hand, as preferred reagents of formula VI a tri-($C_1$-$C_6$-alkyl)silyl chloride, especially trimethylsilyl chloride, or dimethyldichlorosilane. As has already been stated, desferrioxamine B can also be used in the form of a salt, especially an acid addition salt with strong acids (for example those mentioned above), especially hydrogen chloride or methanesulfonic acid, from which the basic material is freed by the basic-reacting reaction medium.

The silylation is carried out under conditions that are generally customary for this reaction, for example at temperatures ranging from the freezing point to the boiling point of the reaction mixture, such as from approximately $-10°$ to approximately $+80°$, preferably from $0°$ to room temperature, preferably under atmospheric pressure and in heterogeneous phase (such as a suspension) while stirring or shaking or, especially, in homogeneous phase in an organic solvent and customarily with an excess of silylating agent, and in the presence of acid-binding inorganic or organic solvents. Suitable solvents are, for example, aprotic organic solvents of relatively low polarity, such as aliphatic and aromatic hydrocarbons of the pentane, hexane, heptane and cyclohexane type or of the benzene, toluene and xylene type, and also halogenated, especially chlorinated, aliphatic hydrocarbons, such as chloroform and dichloromethane, and especially polar aprotic solvents, such as aliphatic and cyclic ethers, for example diethyl ether, 1,2-dimethoxyethane and diisopropyl ether, and dioxan and tertrahydrofuran, respectively, lower aliphatic esters and amides, such as ethyl acetate and formamide, acetamide, N,N-dimethylacetamide and dimethylformamide respectively, and also acetonitrile, dimethyl sulfoxide and hexamethylphosphorus triamide; suitable acid-binding agents are especially organic nitrogen-containing bases, for example tertiary amines of the triethylamine, ethyldiisopropylamine, N,N-dimethylaniline, N-ethylpiperidine or N,N'-dimethylpiperazine type, or aromatic heterocyclic bases of the pyridine, collidine, quinoline or 4-dimethylaminopyridine type.

The starting materials of formula II can, as has already been mentioned, be used directly for the N-acylation without first being isolated from the reaction mixture; if desired, however, they can be obtained in individual form by customary separation methods, such as distillation, chromatography and crystallisation.

The invention relates also to the multi-step process for the manufacture of compounds of formula I in which first of all a compound of formula V is silylated, the resulting compound of formula II is acylated and then the silyl groups still present are removed.

The following Examples illustrate the present invention without limiting the scope thereof in any way. Temperatures are in degrees Celsius (°C).

In the following Examples, Carbowax is the Trademark of Messrs Union Carbide, U.S.A., for polyethyleneglycol monoether. The numerical data in the more precise description, for example Carbowax MPEG 550, indicates the rough average molecular weight. Carbowax MPEG 550 is a mixture of polyethylene glycol-ω-monomethyl ethers that on average contains 12 units of the formula —$CH_2$—$CH_2$—O—. Analogously, Carbowax MPEG 750 is a mixture of polyethyleneglycol-ω-monomethyl ethers with on average 16 ethyleneoxy units.

EXAMPLE 1

N-palmitoyl-desferrioxamine B 126 ml (100 mmol) of trimethylchlorosilane (TMCS) are added over a period of 10 minutes to a suspension of 66 g (100 mmol) of desferrioxamine B-methanesulfonate in 1000 ml of pyridine and the whole is stirred for 3 hours at room temperature. Then, over a period of 10 minutes, 30 g (110 mmol) of palmitoyl chloride are added at below 30° C. and the whole is stirred for a further 19 hours at room temperature. By adding 300 ml of methanol to the reaction mixture, first of all the solids dissolve but, after a few minutes, the desired title compound begins to separate out in the form of crystals.

The crystalline material is recrystallised from 1000 ml of propanol/water (1:1). To remove residual palmitic acid, the crystallisate is digested with diethyl ether, filtered and dried under a high vacuum; m.p. 186°–187° C.

EXAMPLE 2

N-[2-(2-methoxyethoxy)-ethoxycarbonyl]-desferrioxamine B 1.3 ml (10 mmol) of trimethylchlorosilane (TMCS), followed after 5 minutes at 23° C. under an argon atmosphere by 201 mg (1.1 mmol) of chloroformic acid 2-(2-methoxyethoxy)-ethyl ester in 1.0 ml of toluene, are added to a suspension of 657 mg (1 mmol) of desferrioxamine B-methanesulfonate in 12 ml of pyridine. The reaction mixture is stirred for 3 days at room temperature under argon. Excess reagents are destroyed by the addition of 10 ml of methanol and the solvents are distilled off. The residue is dried under a high vacuum and crystallised from water; m.p. 142°–144°.

EXAMPLE 3

N-[ω-methoxy-(dodecakis-ethyleneoxy)-carbonyl]-desferrioxamine B, in which "dodecakis-ethyleneoxy" denotes a radical of the formula ($CH_2$—$CH_2$—O—)$_n$ in which n has an average value of 12

194.0 ml (1500 mmol) of trimethylchlorosilane are added at room temperature to a suspension of 86.5 g (132 mmol) of desferrioxamine B-methanesulfonate in 2000 ml of pyridine and the whole is then stirred for 3 hours at room temperature. The acylating agent, prepared by mixing a solution of 72.6 g (132 mmol) of Carbowax MPEG 550 [$CH_3$—O—($CH_2$—$CH_2$—O—)$_n$H in which n has an average value of 12] in 1000 ml of toluene with 66.0 ml (132 mmol) of a 20% solution of phosgene in toluene at 70° C., stirring the mixture for three hours at that temperature and cooling, is added dropwise to the rection mixture over a period of 15 minutes at room temperature. The mixture is stirred overnight at room temperature, excess reagents are destroyed and silyl groups removed by the addition of 2000 ml of methanol, and the solvents are then distilled off as far as possible. The residue, still containing a substantial amount of pyridine, is crystallised from approximately 500 ml of methyl chloride and 1000 ml of diethyl ether and dried overnight under a high vacuum. The individual title compound with 12 repeating ethyleneoxy groups is obtained from the crude crystalline by chromatography on Sephadex ® LH20; m.p. 131°–132° after crystallisation from ethyl acetate with a small amount of methylene chloride.

EXAMPLE 4

N-[ω-methoxy-(heptadecakis-ethyleneoxy)carbonyl]-desferrioxamine B of formula I, in which "heptadecakis-ethyleneoxy" denotes a radical of the formula ($CH_2$—$CH_2$—O—)$_n$ in which n has an average value of 17

Under the same conditions and with the same amounts of components as in Example 3, desferrioxamine B-methanesulfonate is silylated and then treated with an acylating reagent prepared analogously to Example 3 from 99.0 g (132 mmol) of Carbowax MPEG 750 [$CH_3$—O—($CH_2$—$CH_2$—O)$_n$H, in which n has an average value of 17], in 1000 ml of toluene and 66.0 ml (132 mmol) of 20% phosgene in toluene. The procedure described in Example 3 yields the title compound, m.p. 125°–126°.

EXAMPLE 5

N-[ω-methoxy-(dodecakis-ethyleneoxy)-carbonyl]-desferrioxamine B, in which "dodecakis-ethyleneoxy" denotes a radical of the formula ($CH_2$—$CH_2$—O—)$_n$ in which n has an average value of 12, prepared with a different reagent In a manner analogous to that described in Example 3, 6.56 g (10 mmol) of desferrioxamine B-methanesulfonate in 150 ml of pyridine are silylated with 15.5 m. (120 mmol) of trimethylchlorosilane and reacted with an acylation reagent prepared as follows: 1.78 g (11 mmol) of di-(1-imidazolyl)-carbonyl is added to a solution of 5.5 g (10 mmol) of Carbowax MPEG 550 in 50 ml of toluene, stirred for 1 hour at 70° C. and cooled. Working up in accordance with Example 3 yields the title compound, which is identical to that of Example 3.

EXAMPLE 6

N-(ethoxycarbonylmethylcarbamoyl)-desferrioxamine B of formula I in which
Ac=$C_2H_5$—O—CO—$CH_2$—NH—CO— and
$A^1 = A^2 = A^3 = H$ In a manner analogous to that described in Example 1, 26.3 g (40 mmol) of desferrioxamine B-methylanesulfonate in 300 ml of pyridine are silylated with 50.0 ml (400 mmol) of trimethylchlorosilane (TMCS). After 2.5 hours, 9.3 g (72 mmol) of isocyanatoacetic acid ethyl ester are added to the reaction solution over a period of 10 minutes at 22° C. and the whole is stirred for a further 6 hours a room temperature. By adding 150 ml of methanol excess reagents are destroyed and the silyl groups are removed. The solvents are removed by distillation. The solid residue is dried under a high vacuum and crystallised first from water and then from methanol/dichloromethane; m.p. 177°–178° C.

EXAMPLE 7

N-(methoxysulfonylcarbamoyl)-desferrioxamine B

In a manner analogous to that described in Example 1, 6.56 g (10 mmol) of desferrioxamine B-methanesulfonate in 150 ml of pyridine are silylated with 15.5 ml (120 mmol) of trimethylchlorosilane and, after 1 hour at room temperature, 0.95 ml (11 mmol) of chlorosulfonylisocyanate is added and the whole is stirred for 3 hours at room temperature. By adding methanol excess reagents are destroyed, the silyl groups are removed and the chlorosulfonyl group is converted into the methoxysulfonyl group. The reaction mixture is concentrated to dryness. The residue is dried under a high vacuum and purified by chromatography of Sephadex ® LH 20.

The product is homogeneous according to high pressure liquid chromatography (HPLC=high pressure liquid chromatography) under the following conditions: column (4.0×120 mm) Hypersil ® ODS; solvents: A - 5 millimolar phosphate buffer pH 3.0, B - 20:80 mixture (v/v) of buffer A and acetonitrile; gradient (minutes/solution A:solution B): 0/100:0; 10/60:40; 12/0:100; 14/100:0; 15/100:0; flow rate: 2.3 ml/minute.

Under these conditions the retention time RT=7.13 min compared with RT=8.50 min for desferrioxamine B as standard.

EXAMPLE 8

N-[ω-methoxy-(dodecakis-ethyleneoxy)-carbonylaminosulfonyl]-desferrioxamine B, in which "dodecakis-ethyleneoxy" denotes a radical of the formula ($CH_2$—$CH_2$—O—)$_n$ in which n has an average value of 12

In an analogous manner to and with the same amounts of substance as in Example 5, desferrioxamine B-methanesulfonate is silylated and then reacted with an acylating agent prepared as follows:

0.95 ml (11 mmol) of chlorosulfonylisocyanate is added to a solution of 5.5 g (10 mmol) lof Carbowax MPEG 550 [$CH_2$—O—($CH_2$—$CH_2$—O—)$_n$H in which n has an average value of 12] in 50 ml of toluene and the whole is stirred at 70° C. for 1 hour and cooled. After adding 2000 ml of methanol the reaction mixture is concentrated to dryness. The residue (containing a substantial amount of pyridine) is crystallised from approximately 500 ml of methylene chloride and 1000 ml of diethyl ether and dried overnight under a high vacuum. A further purification can be carried out by chromatography on Sephadex ® LH 20.

Under the conditions indicated in Example 7, the product is homogeneous according to HPLC; RT=10.25 min compared with RT=8.50 min for desferrioxamine B as standard.

What is claimed is:

1. A process for the manufacture of a compound of formula I

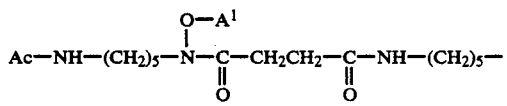 (I)

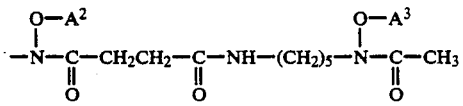

in which Ac is $C_2$-$C_{20}$-alkanoyl, benzoyl, $C_{18}$-alkenoyl, ($C_1$-$C_{12}$-alkoxy)carbonyl, a radical of the formula —CO—O—($CH_2$—$CH_2$—O—)$_n$-lower alkyl in which n is from 1 to 19, chlorocarbonyl, (1-imidazolyl)-carbonyl, N-di-lower alkylcarbamoyl, N-($C_1$-$C_5$-alkyl)-carbamoyl substituted in the 1- or 2-position of the alkyl moiety by ($C_1$-$C_4$-alkoxy)-carbonyl, N-(chlorosulfonyl)-carbamoyl, N-(lower alkoxysulfonyl)-darbamoyl or a radical of the formula —$SO_2$—N—H—CO(—O—$CH_2$—$CH_2$)$_n$-lower alkoxy in which n is from 0 to 19, and $A^1$, $A^2$ and $A^3$ are each hydrogen, characterized in that a compound of formula II

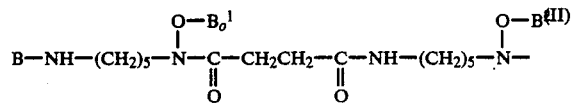

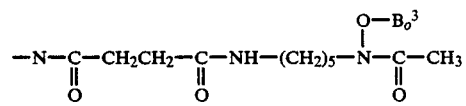

in which each pf B, $B_o^1$, $B_o^2$ and $B_o^3$ is an organic silyl group (sil) of formula

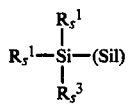

wherein $R_s^1$ and $R_s^2$, independently of one another, are each $C_1$-$C_8$-alkyl, phenyl, p-tolyl, benzyl or phenethyl and $R_s^3$ is $C_1$-$C_8$-alkyl, phenyl, p-tolyl, benzyl, phenethyl or chlorine, is reacted with an acylating agent selected from the group consisting of (1) $Ac^4Y$, wherein $Ac^4$ is $C_2$-$C_{20}$-alkanoyl, benzoyl, $C^{18}$-alkenoyl, ($C_1$-$C_{20}$-alkoxy)-carbonyl, a radical of the formula —CO—O—($CH_2$—$CH_2$—O—)$_n$-lower alkyl in which n is from 1 to 19, chlorocarbonyl, (1-imidazolyl)carbonyl, N-di-lower alkylcarbamoyl, N-($C_1$-$C_5$-alkyl)-carbamoyl substituted in the 1- or 2-position of the alkyl moiety by ($C_1$-$C_4$-alkoxy)carbonyl, or a radical of the formula —$SO_2$—NH—CO(—O—$CH_2$—$CH_2$)$_n$-lower alkoxy in which n is from 0 to 19, and Y is chlorine, 1-imidazolyl, bromine or azido, (2) chlorosulfonylisocyanate, (3) $R^4$—N=C=O wherein $R^4$ is $C_1$-$C_5$-alkyl substituted in the 1- or 2-position of the alkyl moiety by ($C_1$-$C_4$-alkoxy)-carbonyl, (4) $Ac^5$—O—$Ac^5$, wherein $Ac^5$ is $C_2$-$C_{20}$-alkanoyl, benzoyl, $C_{18}$-alkenoyl, ($C_1$-$C_{12}$-alkoxy)-carbonyl, a radical of the formula —CO—O—($CH_2$—$CH_2$—O—)$_n$-lower alkyl in which n is from 1 to 19, chlorocarbonyl, and (5) $R^3$=C=O wherein $R^3$ is $C_2$-$C_{20}$-alkylidene or $C^{18}$-alkenylidene, and solvolytically splitting off the O-bonded organic silyl groups Sil present by treatment with a lower alkanol.

2. A process according to claim 1 wherein a starting material of formula II in which each of B, $B_o^1$, $B_o^2$ and $B_o^3$ are either dimethylchlorosilyl or trimethylsilyl, is used.

3. A process according to claim 1 wherein an acylating agent of the formula $Ac^4Y$ in which $Ac^4$ has the formula $R^o$—O—CO— wherein $R^o$ is $C_1$-$C_{20}$-alkyl or a radical of the formula —($CH_2$—$CH_2$—O—)$_n$-lower alkyl in which n is from 1 to 19, and Y is chlorine, is used.

4. A process according to claim 1 wherein an acylating agent of the formula $Ac^4Y$ in which $Ac^4$ has the formula

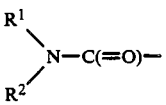

wherein $R^1$ and $R^2$, independently of one another are each lower alkyl, or wherein $R^1$ is hydrogen and $R^2$ is $C_1$-$C_5$-alkyl substituted in the 1-position by $C_1$-$C_4$-alkoxycarbonyl, and in which Y is chlorine, is used.

5. A process according to claim 1 wherein an acylating agent of the formula $Ac^4Y$ in which $Ac^4$ is a radical of the formula lower alkoxy-($CH_2$—$CH_2$—O—)$_n$-CO—NH—$SO^2$— in which n is from 1 to 19, and Y is bromine or chlorine, is used.

6. A process according to claim 1 wherein an acylating agent of the formula $R^4$—N=C=O in which $R^4$ is $C_1$-$C_5$-alkyl that is unsubstituted or substituted in the 1-position by $C_1$-$C_4$-alkoxycarbonyl, is used.

7. A process according to claim 1 wherein chlorosulfonylisocyanate is used as an acylating agent.

8. A process according to claim 1 wherein phosgene or bis-1-imidazolyl)-carbonyl is used an acylating agent $Ac^4Y$.

9. A process according to claim 1 wherein there is used as an acylating agent $Ac^4Y$ an acid chloride selected from the group consisting of $C_2$-$C_{20}$-alkanoic acid chloride, benzoyl chloride, $C_{18}$-alkenoic acid chloride, chloroformic acid ($C_1$-$C_{12}$-alkyl)-ester, a chloroformic acid ester of the formula Cl—CO—O—($CH_2$—$CH_2$—O—)$_n$-lower alkyl in which n is from 1 to 19, or a chloroformic acid ester of the formula Cl—CO—NH—($C_1$-$C^5$-alkylene)—COO—($C_1$-$C_4$-alkyl) wherein the —COO—($C_1$-$C_4$-alkyl)-substituent is located in the 1- or 2-position of the alkylene-moiety.

10. A process according to claim 1 wherein the starting material of formula II B, $B_o^1$, $B_o^2$ and $B_o^3$ are the same.

* * * * *